United States Patent [19]

Cook

[11] Patent Number: 5,231,099
[45] Date of Patent: Jul. 27, 1993

[54] USE OF SIGMA RECEPTOR ANTAGONISTS TO ENHANCE THE EFFECTS OF ANTIPSYCHOTIC DRUGS

[75] Inventor: Leonard Cook, Newark, Del.

[73] Assignee: Du Pont Merck Pharmaceutical Company, Wilmington, Del.

[21] Appl. No.: 685,749

[22] Filed: Apr. 15, 1991

[51] Int. Cl.$^5$ .............................................. A61K 31/44
[52] U.S. Cl. ................................................... 514/279
[58] Field of Search ......................................... 514/279

[56] References Cited

U.S. PATENT DOCUMENTS

| 4,232,037 | 11/1980 | Florvall et al. | 514/255 |
| 4,400,383 | 8/1983 | Davidson et al. | 514/255 |
| 4,588,728 | 5/1986 | Ferris | 514/255 |

FOREIGN PATENT DOCUMENTS

| 11606 | 5/1980 | European Pat. Off. . |
| 337136 | 10/1989 | European Pat. Off. . |
| 2358881 | 7/1976 | France . |
| 83/03541 | 10/1983 | PCT Int'l Appl. . |

OTHER PUBLICATIONS

Ferris et al., J. Pharm. Pharmacol. 1982, 34:388.
Ferris et al., Life Sciences, 1986, 38:2329.
Ogren et al., Eur. J. Pharm. 1984, 102:439.
Snyder and Largent, J. Neuropsyc. 1989, 1:7.
Taylor and Dekleva, Drug Dev. Res. 1987, 112:65.

Primary Examiner—S. J. Friedman
Attorney, Agent, or Firm—Blair Q. Ferguson

[57] ABSTRACT

The invention relates to a method of treating psychosis in a mammal which comprises administering to the mammal an effective amount of a dopamine receptor antagonist antipsychotic and a sigma receptor antagonist having greater affinity for sigma receptors than for dopamine receptors, in an amount effective to selectively enhance the antipsychotic effects of the dopamine receptor antagonist relative to the adverse side effects of the dopamine receptor antagonist.

8 Claims, 1 Drawing Sheet

USE OF SIGMA RECEPTOR ANTAGONISTS TO ENHANCE THE EFFECTS OF ANTIPSYCHOTIC DRUGS

BACKGROUND OF THE INVENTION

Schizophrenia is a psychosis marked by withdrawn, bizarre, and sometime delusional behavior. About 1% of the United States population, 2,400,000 people, suffer from the disease. The estimated medical costs in the United States for treatment of schizophrenia run as high as $40 billion a year.

Several classes of drugs are currently marketed for use in the symptomatic treatment of psychoses. Certain antipsychotics, referred to as neuroleptics, are known to produce unwanted extrapyramidal side effects, including acute dystonia, akathisia, parkinsonian syndrome, anticholinergic effects, hypotension, increased prolactin levels, malignant syndrome, perioral tremor, and tardive dyskinesia. The parkinsonian syndrome and tardive dyskinesia side effects are thought to be mediated by the antagonist effect of the drug on dopamine receptors (Goodman and Gilman's The Pharmacological Basis of Therapeutics, 8th Edition, Pergamon Press, 1990). Tardive dyskinesia, an often irreversible syndrome consisting of involuntary movement or rigidity of the muscles, is caused by standard neuroleptics at an estimated rate of 4 cases per 100 patient years of treatment.

Because of the limitations of currently available antipsychotic drugs, the search continues for compounds with fewer deleterious side effects and better efficacy (Abou-Gharbia and Moyer, "Novel Antipsychotic Agents", in Annual Reports in Medicinal Chemistry, Volume 25, pp 1-10, Academic Press, 1990).

Effective neuroleptics include the phenothiazine derivatives chlorpromazine hydrochloride (Thorazine), triflupromazine hydrochloride (Vesprin), mesoridazine besylate (Serentil), thioridazine hydrochloride (Mellaril, Millazine), acetophenazine maleate (Tindal), fluphenazine (Permitil, Prolixin), perphenazine (Trilafon), trifluoperazine hydrochloride (Stelazine, Suprazine), chlorprothixene (Taractan), and thiothixene hydrochloride (Navane). Other antipsychotics include haloperidol and haloperidol decanoate (Haldol, Halperon), loxapine succinate (Loxitane), molindone hydrochloride (Moban), and pimozide (Orap). The pharmacology of these drugs is reviewed in Goodman and Gilman's The Pharmacological Basis of Therapeutics, 8th Edition, Pergamon Press, 1990 and in Physicians' Desk Reference, 45th Edition, Medical Economics, 1991.

Antipsychotics also include "atypical" antipsychotics, such as the dibenzodiazepine clozapine (Clozaril), which have little extrapyramidal side effects.

Neuroleptic drugs, which are the primary antipsychotic drugs used in the treatment of schizophrenia, are thought to exert their therapeutic effects by binding to and blocking dopamine receptors, primarily $D_2$ receptors (Snyder and Largent (1989) J. Neuropsychiatry 1:7-15). Most marketed antipsychotics are neuroleptics and are referred to as dopamine receptor antagonist antipsychotics. Some neuroleptics, such as cinuperone, tiospirone, and haloperidol, are known to nonselectively antagonize both sigma and dopamine $D_2$ receptors (Snyder and Largent (1989) J. Neuropsychiatry 1:7-15).

SUMMARY OF THE INVENTION

In the present invention, sigma receptor antagonists having greater affinity for sigma receptors than for dopamine receptors were discovered to enhance the antipsychotic effects of dopamine receptor antagonist antipsychotics relative to the adverse side effects of the dopamine receptor antagonist antipsychotic. It has been discovered that sigma receptor antagonists with greater affinity for sigma receptors than dopamine receptors will selectively potentiate the measures of psychotherapeutic properties of dopamine receptor antagonist antipsychotics and will not potentiate the measures reflecting unwanted short and long-term neurological side effects produced by these dopamine receptor antagonist antipsychotics, such as extrapyramidal symptoms or tardive dyskinesia.

The present invention, therefore, provides a means of maintaining or enhancing the psychotherapeutic properties of a dopamine receptor antagonist antipsychotic drug without enhancing their usual neurological side effects. This can be accomplished by employing lower doses of the dopamine receptor antagonist antipsychotic when administered in combination or concurrently with a sigma receptor antagonist having greater affinity for sigma receptors than for dopamine receptors.

The method of the present invention improves the therapeutic ratio of classical dopamine receptor antagonist antipsychotics and also offers the potential of a broader therapeutic profile by the combination of the therapeutic properties of a sigma receptor antagonist with the therapeutic properties of a dopamine receptor antagonist antipsychotic, when administered in combination or concurrently with a sigma receptor antagonist having greater affinity for sigma receptors than for dopamine receptors.

Effective dopamine receptor antagonist antipsychotics useful in the method of the invention include the phenothiazine derivatives chlorpromazine hydrochloride (Thorazine), triflupromazine hydrochloride (Vesprin), mesoridazine besylate (Serentil), thioridazine hydrochloride (Mellaril, Millazine), acetophenazine maleate (Tindal), fluphenazine (Permitil, Prolixin), perphenazine (Trilafon), trifluoperazine hydrochloride (Stelazine, Suprazine), chlorprothixene (Taractan), thiothixene hydrochloride (Navane). Other antipsychotics include haloperidol and haloperidol decanoate (Haldol, Halperon), loxapine succinate (Loxitane), molindone hydrochloride (Moban) and pimozide (Orap). The pharmacology, including dosage and formulation, of these drugs is reviewed in Goodman and Gilman's The Pharmacological Basis of Therapeutics, 8th Edition, Pergamon Press, 1990 and in Physicians' Desk Reference, 45th Edition, Medical Economics, 1991.

Sigma receptor antagonists having greater affinity for sigma receptors than for dopamine receptors include compounds having an inhibition constant, $K_i$, of 500 nM or less for sigma receptors and having at least a 5-fold greater affinity for sigma receptors relative to dopamine receptors. The sigma receptor antagonists useful in the present invention preferably have a $K_i$ for sigma receptors of less than 100 nM and at least a 50 to 100-fold greater affinity for sigma receptors than for dopamine receptors.

Unlike neuroleptics, the sigma receptor antagonists useful in the method of the present invention lack or have relatively weak dopamine receptor-blocking activity and, unlike neuroleptics, elicit their effects primarily without directly antagonziing the dopamine receptor system.

The sigma receptor antagonist compounds useful in this invention includes (N-phthalimidoalkyl) piperidines of the formula:

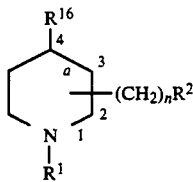  (I)

or a pharmaceutically acceptable salt or an N-oxide thereof wherein:

a is a single or double bond, provided that when a is a double bond then $R^2(CH_2)_nR^2$ is attached at C-4;

n is 0–4, provided that when $(CH_2)_nR^2$ is attached to the 2-position of the piperidine ring then n is 2–4;

$R^1$ is $(CH_2)_mR^3$ or $(CH_2)_pAr$, where m is 1–4 and p is 1–4;

$R^2$ is

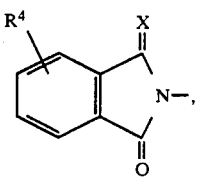

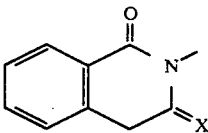

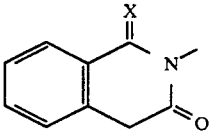

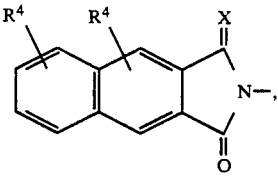

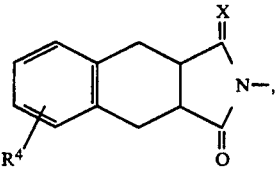

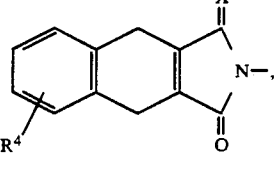

-continued

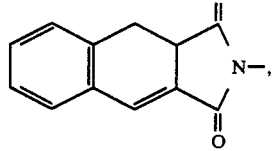

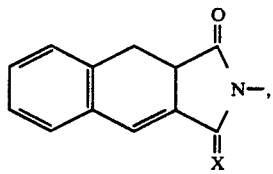

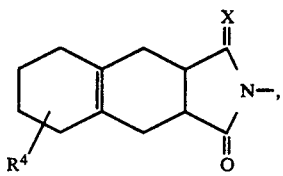

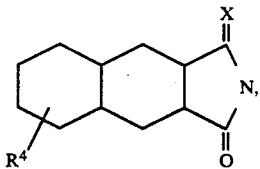

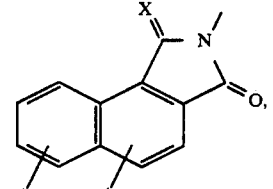

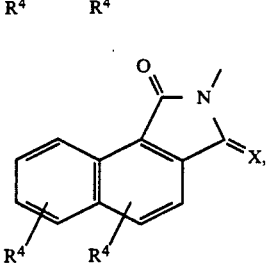

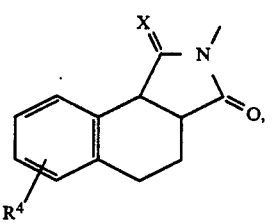

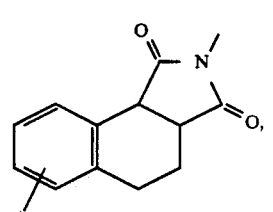

-continued
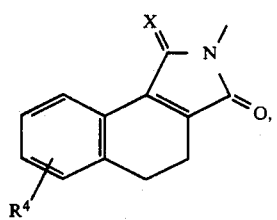
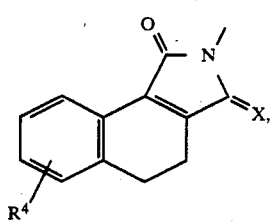
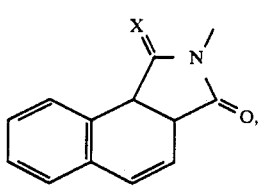
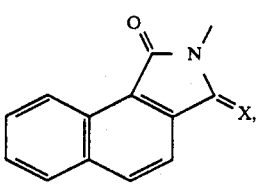
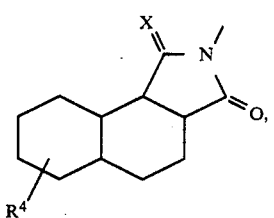
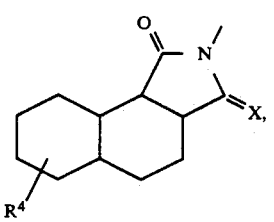
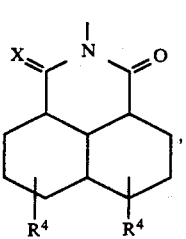
-continued
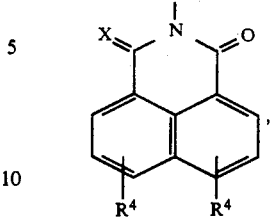
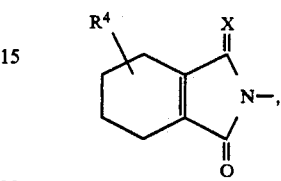
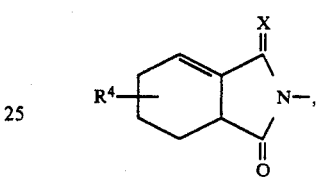
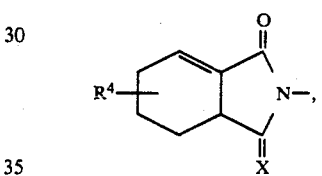
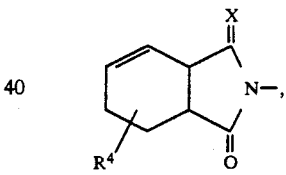
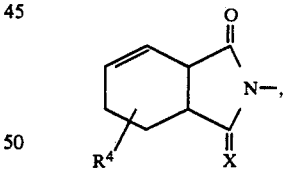
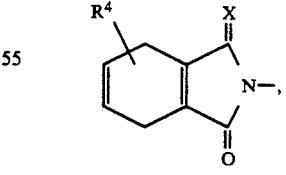
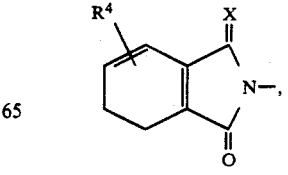

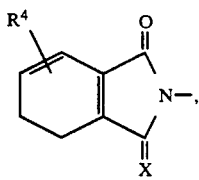
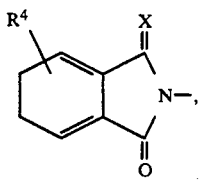
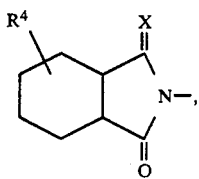
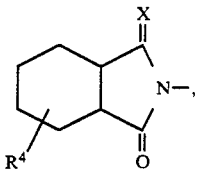
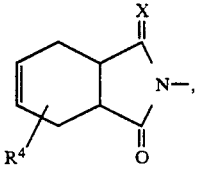
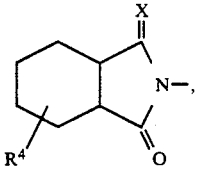
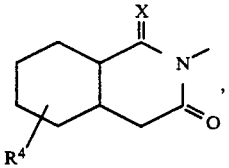
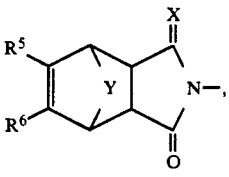
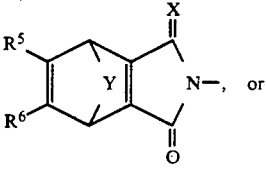

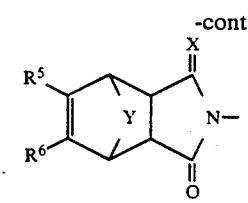

$R^3$ is cycloalkyl of 3 to 8 carbon atoms;

$R^4$ is 1–4 substituents independently selected from the group consisting of H, halogen, $NO_2$, $NH_2$, haloalkyl of 1 to 3 carbon atoms and 1 to 7 halogen atoms, $C_1$-$C_3$ alkyl, $NHCOR^7$, NHCO-phenyl, OH, $OR^8$ and Ar';

$R^5$ an $R^6$ independently are H, alkyl of 1 to 3 carbon atoms, Ar" or taken together are —CH=CH—CH=CH—;

$R^7$ and $R^8$ independently are H or alkyl of 1 to 3 carbon atoms;

X is O, $H_2$; H, OH; $R^9$, OH; Ar''', OH; H, $R^9$; or H, $OR^9$;

Y is $CH_2$, $CHR^{10}$, $C(R^{10})_2$, O, $CH_2CH_2$, $(CH_2)_3$,

Ar, Ar', Ar" and Ar''' independently are phenyl optionally substituted with 1–5 substituents independently selected from the group consisting of: H, halogen, OH, alkoxy of 1 to 3 carbon atoms, $NR^{11}R^{12}$, SH, $S(O)_tR^{13}$, where t is 0–2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, naphthyl, pyridyl, pyrimidyl, quinolyl or isoquinolyl;

$R^9$ and $R^{10}$ independently are alkyl of 1 to 3 carbon atoms;

$R^{11}$-$R^{15}$ independently are H or alkyl of 1 to 3 carbon atoms;

$R^{16}$ is H; OH; O-alkyl of 1–6 carbons; O-acyl of 1–8 carbons; alkyl of 1–12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6–12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6–12 carbons); 2- and 3- pyrrolyl; 2- and 3- furyl; 2- and 3- thienyl; 2,3, and 4-pyridyl; 2- and 3-benzofuryl; 2- and 3- indolyl; 2- and 3-benzothienyl; 2, 3, and 4- quinolyl; and 1, 3, and 4-isoquinolyl; with the following provisos:

(1) when $R^1$ is $(CH_2)_pAr$ (where p is 1); $R^2$ is

and $(CH_2)_nR^2$, (n=O), is attached at the C-4 position on the piperidine ring; then X cannot be $H_2$ or O.

(2) $R^{16}$ is H, OH, alkyl or aryl when $(CH_2)_nR^2$ is attached to the 4-position of the piperidine ring.

Some compounds useful in the present invention can exist as optical isomers and both the racemic mixtures of these isomers as well as the individual optical isomers which confer activity are within the scope of compounds useful in the present invention. In addition some compounds useful in the present invention can exist as cis or trans isomers and although these are not all specifically set forth, the cis and trans fused compounds as known to those skilled in the art, are within the scope of this invention. Preferred compounds useful in the method of the present invention are compounds of Formula (I) for which one or more of the following occur: n is 1-4; $R^1$ is $(CH_2)_pAr$; p is 1-2; $R^2$ is

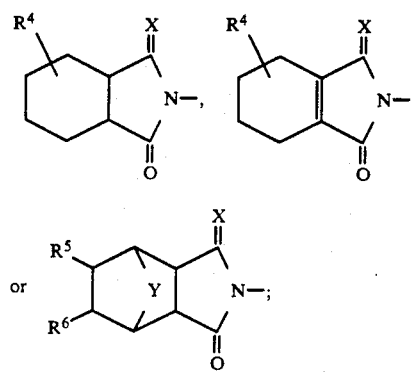

$(CH_2)_nR^2$ is attached at the C-4 position of the piperidine ring;

X is O or $H_2$;

$R^4$, $R^5$ and $R^6$ are all H;

Ar is phenyl; or

Y is $(CH_2)_3$ or O.

More preferred compounds useful in the present invention are the compounds of formula (I) wherein n is 1.

The selective sigma receptor antagonist compounds useful in the present invention also include cycloalkylpiperidines of the formula:

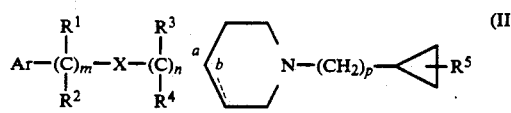

or a pharmaceutically acceptable salt thereof, wherein:
m is 0 to 3;
n is 0 to 3;
provided that m and n are not both O;
p is 0 to 3;

or CHOH;

$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;

$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;

provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;

$R^5$ is H, alkyl, halogen, OH or alkenyl;

$R^6$ is H, alkyl of 1 to 5 carbon atoms or $Ar^1$;

Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3
carbon atoms, haloalkyl of 1 to 3 carbon atoms and 1 to 7 halogen atoms, SH, S(O)t alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;

$Ar^2$ is naphthyl or phenyl optionally substituted with alkyl of 1 to 3 carbon atoms, haloalkyl
of 1 to 3 carbon atoms and 1 to 7 halogen atoms, alkoxy of 1 to 3 carbon atoms, halogen or alkylthio of 1 to 3 carbon atoms;

$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and a or b is a double bond or a single bond, provided that both are not double bonds.

Preferred compounds useful in the present invention include those compounds of Formula (II) wherein:
X is C(O), CHOH or O;
m is 0;
n and p are 1;
$R^3$-$R^5$ are H; and/or
Ar is phenyl optionally substituted with halogen, $OCH_3$, $NH_2$, $NO_2$ or another phenyl group.

Pharmaceutical compositions comprising an effective amount of a compound of Formula I or II and a pharmaceutically acceptable carrier are useful in the method of the present invention.

Other sigma receptor antagonists lacking or having relatively weak dopamine receptor-blocking activity are expected to be useful in the method of the invention. Examples of other sigma receptor antagonists lacking or having weak dopamine receptor-blocking activity and expected to be useful in this invention are rimcazole (also known as BW234U) (Ferris et al. (1982) J. Pharm. Pharmacol. 34: 388-390; Ferris et al. (1986) Life Sciences 38: 2329-2337; U.S. Pat. No. 4,400,383; U.S. Pat. No. 4,588,728), remoxipride (Ogren et al. (1984) European Journal of Pharmacology 102: 439-474; U.S. Pat. No. 4,232,037; Snyder and Largent (1989) J. Neuropsychiatry 1: 7-15), and BMY14802 (Taylor and Dekleva (1987) Drug Development Research 11: 65-70; U.S. Pat. No. 4,605,655). The above identified patents are hereby incorporated by reference.

Other sigma receptor antagonists lacking or having relatively weak dopamine receptor-blocking activity and expected to be useful in the method of the invention include the compounds claimed in copending, commonly assigned U.S. Pat. application Ser. No. 07/506961, filed Mar. 28, 1990 and U.S. Pat. application Ser. No. 07/500573, filed Mar. 28, 1990, the disclosures of which are hereby incorporated by reference.

DETAILED DESCRIPTION OF THE INVENTION

Figure 1:
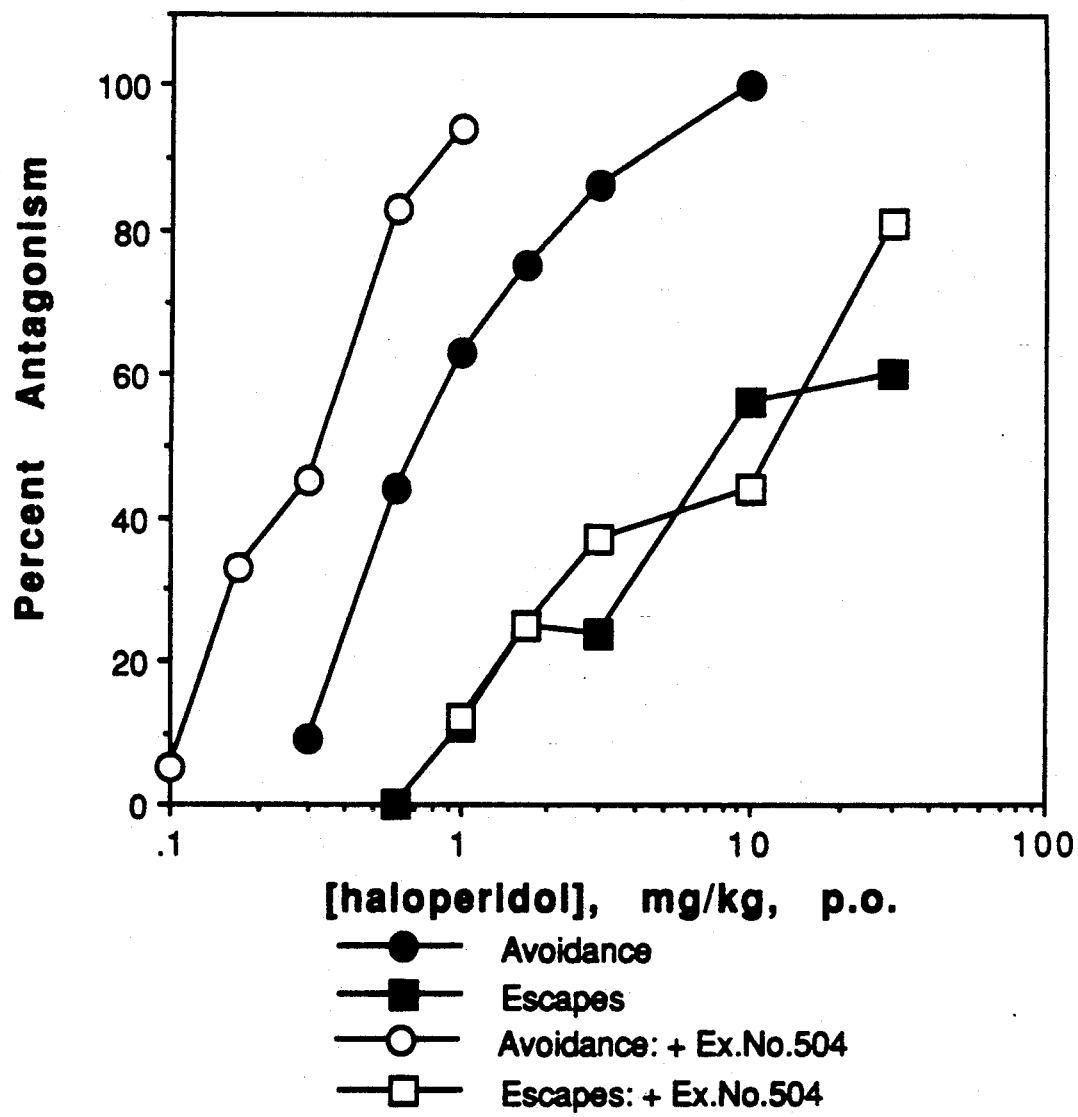
FIG. 1 shows the effect of haloperidol (Haldol) alone and haloperidol (Haldol) + Ex. No. 504 on avoidance behavior and escape behavior in pole climb avoidance in rats.

We have discovered that sigma receptor antagonists having greater affinity for sigma receptors than for dopamine receptors are useful to enhance the antipsychotic effects of dopamine receptor antagonist antipsychotics relative to the adverse side effects of the dopamine receptor antagonist antipsychotic. It has been discovered that sigma receptor antagonists with greater affinity for sigma receptors than dopamine receptors will selectively potentiate the measures of psychotherapeutic properties of dopamine receptor antagonist antipsychotics and will not potentiate the measures reflecting unwanted short and long-term neurological side effects produced by these dopamine receptor antagonist antipsychotics, such as extrapyramidal symptoms or tardive dyskinesia.

The present invention, therefore, provides a means of maintaining or enhancing the psychotherapeutic properties of a dopamine receptor antagonist antipsychotic drug without enhancing their usual neurological side effects. This can be accomplished by employing lower doses of the dopamine receptor antagonist antipsychotic, when administered in combination or concurrently with a sigma receptor antagonist having greater affinity for sigma receptors than for dopamine receptors.

The method of the present invention improves the therapeutic ratio of dopamine receptor antagonist antipsychotics and also offers the potential of a broader therapeutic profile by the combination of the therapeutic properties of a sigma receptor antagonst with the therapeutic properties of a dopamine receptor antagonist antipsychotic.

Effective neuroleptics useful in the method of the invention include the phenothiazine derivatives chlorpromazine hydrochloride (Thorazine), triflupromazine hydrochloride (Vesprin), mesoridazine besylate (Serentil), thioridazine hydrochloride (Mellaril, Millazine), acetophenazine maleate (Tindal), fluphenazine (Permitil, Prolixin), perphenazine (Trilafon), trifluoperazine hydrochloride (Stelazine, Suprazine), chlorprothixene (Taractan), thiothixene hydrochloride (Navane). Other antipsychotics include haloperidol and haloperidol decanoate (Haldol, Halperon), loxapine succinate (Loxitane), molindone hydrochloride (Moban) and pimozide (Orap). The pharmacology, including dosage and formulation, of these drugs is reviewed in Goodman and Gilman's. The Pharmacological Basis of Therapeutics, 8th Edition, Pergamon Press, 1990 and in Physicians' Desk Reference, 45th Edition, Medical Economics, 1991.

Sigma receptor antagonists having greater affinity for sigma receptors than for dopamine receptors useful in the present invention include compounds having an inhibition constant, $K_i$, of 500 nM or less for sigma receptors and having at least a 5-fold greater affinity for sigma receptors relative to dopamine receptors. The sigma receptor antagonists useful in the present invention preferably have a $K_i$ for sigma receptors of less than 100 nM and at least a 50 to 100-fold greater affinity for sigma receptors than for dopamine receptors.

Unlike neuroleptics, the sigma receptor antagonists useful in the method of the present invention lack or have relatively weak dopamine receptor-blocking activity.

Typical dopamine receptor antagonist antipsychotic agents, such as haloperidol and chlorpromazine, produce effects in many behavioral paradigms. Some of these behaviors can be said to be reflective of the therapeutic effects of the drugs based upon correlations with clinical potency and the spectrum of clinically useful agents that demonstrate activity. Other behaviors can be said to be reflective of unwanted sideeffect liability based upon similar correlations. The conditioned avoidance response, in many forms, has been used to predict antipsychotic efficacy. Inhibition of conditioned avoidance is associated with the therapeutic properties of antipsychotics. In contrast, inhibition of conditioned escape behavior has been associated with non-specific sedative effects. The induction of catalepsy by typical antipsychotics is associated with the production of sedative and extrapyramidal sideeffects in man.

Our results indicate that sigma receptor antagonists having greater affinity for sigma receptors than for dopamine receptors will potentiate the therapeutic properties while not effecting the unwanted side-effect properties of dopamine antagonist antipsychotics. These results have profound significance for the treatment of psychosis since it is the severe side-effects that are the major limitation to the use of typical dopamine receptor antagonist antipsychotics. The addition of a sigma receptor antagonist to treatment with the typical dopamine receptor antagonist antipsychotic is expected to enhance the therapeutic efficacy and therefore produce a greater therapeutic index than the dopamine receptor antagonist antipsychotic alone.

The sigma receptor antagonist compounds useful in this invention include (N-phthalimidoalkyl) piperidines of the formula:

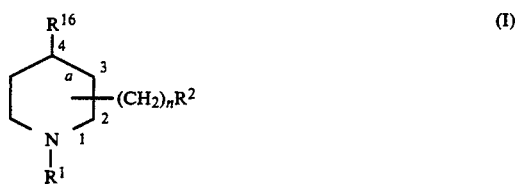

(I)

or a pharmaceutically acceptable salt or an N-oxide thereof wherein:

a is a single or double bond, provided that when a is a double bond then $R^2(CH_2)_n$ is attached at C-4;

n is 0–4, provided that when $(CH_2)_nR^2$ is attached to the 2-position of the piperidine ring then n is 2–4;

$R^1$ is $(CH_2)_mR^3$ or $(CH_2)_pAr$ where m is 1–4 and p is 1–4;

$R^2$ is

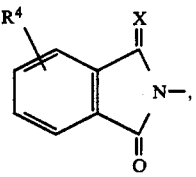

-continued
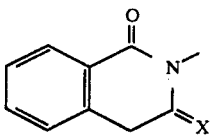
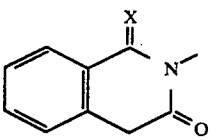
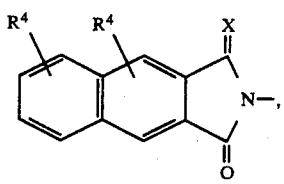
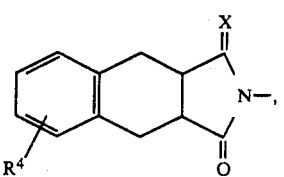
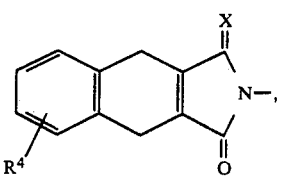
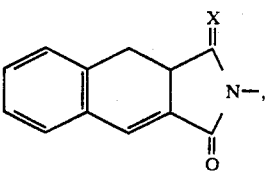
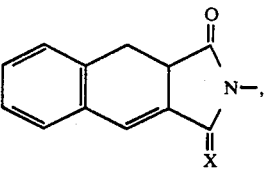
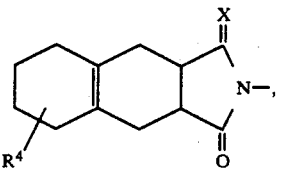
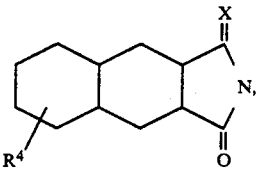
-continued
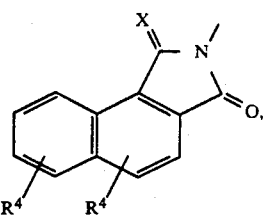
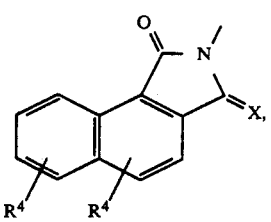
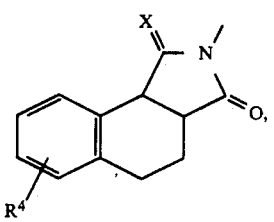
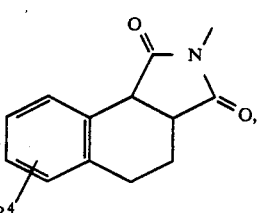
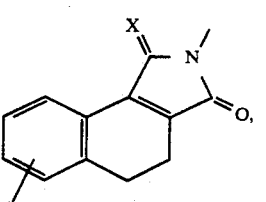
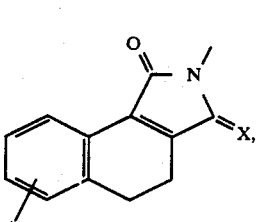
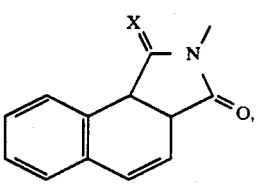

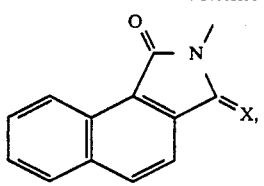
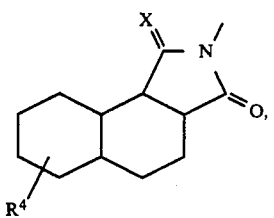
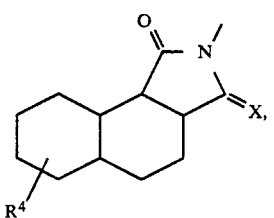
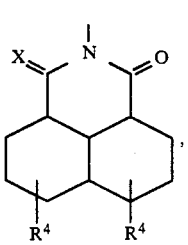
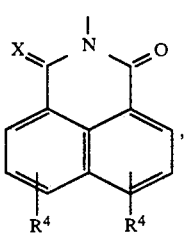
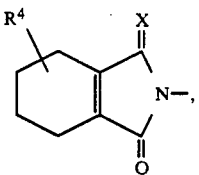
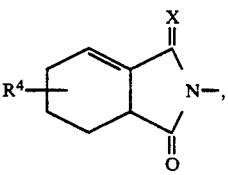
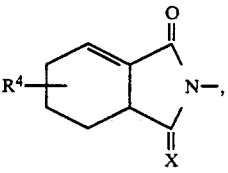
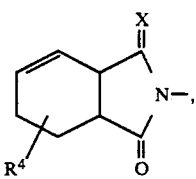
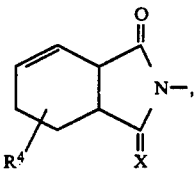
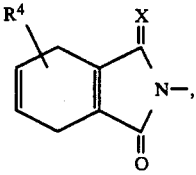
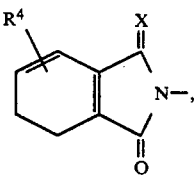
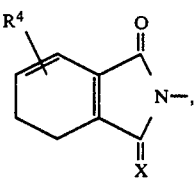
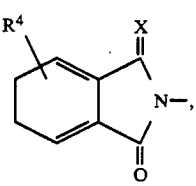
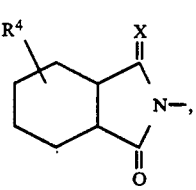
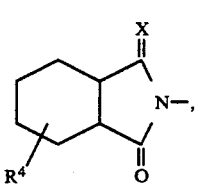
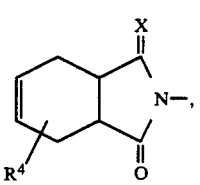

-continued

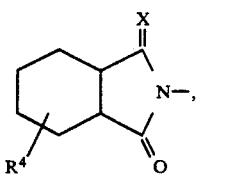

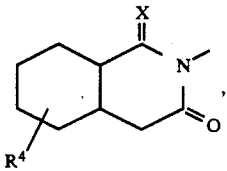

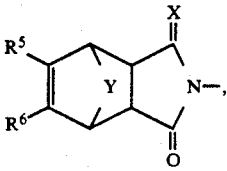

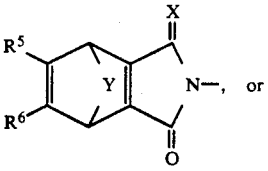

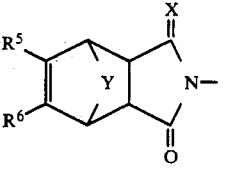

$R^3$ is cycloalkyl of 3 to 8 carbon atoms;

$R^4$ is 1-4 substituents independently selected from the group consisting of H, halogen, $NO_2$, $NH_2$, haloalkyl of 1 to 3 carbon atoms and 1 to 7 halogen atoms, $C_1$-$C_3$ alkyl, $NHCOR^7$, NHCO-phenyl, OH, $OR^8$ and Ar';

$R^5$ and $R^6$ independently are H, alkyl of 1 to 3 carbon atoms, Ar" or taken together are —CH=CH—CH=CH—;

$R^7$ and $R^8$ independently are H or alkyl of 1 o 3 carbon atoms;

X is O; $H_2$; H, OH; $R^9$, OH; Ar"', OH; H, $R^9$; or H, $OR^9$;

Y is $CH_2$, $CHR^{10}$, $C(R^{10})_2$, O, $CH_2CH_2$, $(CH_2)_3$,

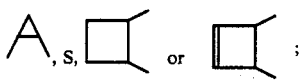

Ar" and Ar''' independently are phenyl optionally substituted with 1-5 substituents independently selected from the group consisting of:

H, halogen, OH, alkoxy of 1 to 3 carbon atoms, $NR^{11}R^{12}$, SH, $S(O)_tR^{13}$, where t is 0-2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, naphthyl, pyridyl, pyrimidyl, quinolyl or isoquinolyl;

$R^9$ and $R^{10}$ independently are alkyl of 1 to 3 carbon atoms;

$R^{11}$-$R^{15}$ independently are H or alkyl of 1 to 3 carbon atoms;

$R^{16}$ is H; OH; O-alkyl of 1-6 carbons; O-acyl of 1-8 carbons; alkyl of 1-12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12-carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12 carbons); 2- and 3- pyrrolyl; 2- and 3- furyl; 2- and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl; with the following provisos:

(1) when $R^1$ is $(CH_2)_pAr$ (where p is 1);
$R^2$ is

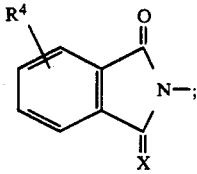

and $(CH_2)_nR^2$, (n=O), is attached at the C-4 position on the piperidine ring; then X cannot be $H_2$ or O.

(2) $R^{16}$ is H, OH, alkyl or aryl when $(CH_2)n$ $R^2$ is attached to the 4-position of the piperidine ring.

Preferred compounds useful in the method of the present invention are compounds of Formula (I) for which one or more of the following occur:

n is 1-4;
$R^1$ is $(CH_2)_pAr$;
p is 1-2;

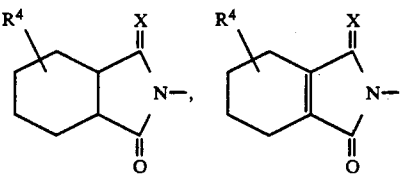

or 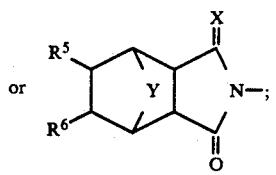

$(CH_2)_nR^2$ is attached at the C-4 position of the piperidine ring;
X is O or $H_2$;
$R^4$, $R^5$ and $R^6$ are all H;
Ar is phenyl; or
Y is $(CH_2)_3$ or O.

More preferred compounds useful in the present invention are the compounds of formula (I) wherein n is 1.

Specifically preferred compounds useful in the present invention are compounds of formula (I) wherein:

(1) $(CH_2)_n R^2$ is attached at the C-4 position of the piperidine ring;
n is 1;
$R^2$ is

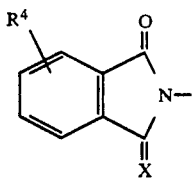

X is O;
$R^4$ is H;
$R^1$ is $(CH_2)_p Ar$;
p is 2; and
Ar is phenyl.

(2) $(CH_2)_n R^2$ is attached at the C-4 position of the piperidine ring;
n is 1;
$R^2$ is

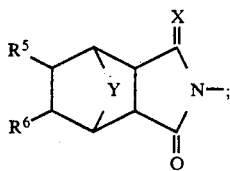

X is O;
Y is $(CH_2)_3$ and $R^5$ and $R^6$ are H;
$R^1$ is $(CH_2)_p Ar$;
p is 2; and
Ar is phenyl.

(3) $(CH_2)_n R_2$ is attached at the C-4 position of the piperidine ring;
n is 1;
$R^2$ is

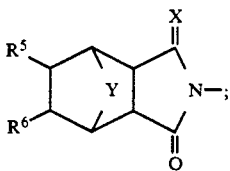

X is O;
Y is O;
$R^5$ and $R^6$ are H;
$R^1$ is $(CH_2)_p Ar$;
p is 2; and
Ar is phenyl.

(4) $(CH_2)_n R^2$ is attached at the C-4 position of the piperidine ring;
n is 1;
$R^2$ is

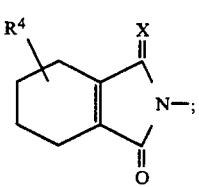

X is $H_2$;
$R^4$ is H;
$R^1$ is $(CH_2)_p Ar$;
p is 2; and
Ar is phenyl.

The selective sigma receptor antagonist compounds useful in the present invention also include cycloalkyl-piperidines of the formula:

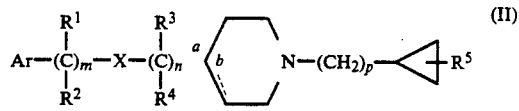

or a pharmaceutically acceptable salt thereof, wherein:
m is 0 to 3;
n is 0 to 3;
provided that m and n are not both 0;
p is 0 to 3;

or CHOH;

$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;

$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;

provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;

$R^5$ is H, alkyl, halogen, OH or alkenyl;
$R^6$ is H, alkyl of 1 to 5 carbon atoms or $Ar^1$;

Ar and $Ar^1$ independently are naphthyl, pyridyl, pyrimidyl, indolyl, quinolinyl, isoquinolinyl,
or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;

$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and a or b is a double bond or a single bond, provided that both are not double bonds.

Preferred compounds useful in the present invention include those compounds of Formula (II) wherein:
X is C(O), CHOH or O;
m is 0;
n and p are 1;
R3–R5 are H; and/or
Ar is phenyl optionally substituted with halogen, $OCH_3$, $NH_2$, $NO_2$ or another phenyl group.

Specifically preferred compounds useful in the present invention are:

(a) 1-(cyclopropylmethyl)-4-(2'-(4"-fluorophenyl)-2'-oxoethyl) piperidine (b) 1-(cyclopropylmethyl)-4-(2'-(4"-fluorophenyl)-2'-oxoethyl) piperidine, hydrobromide salt (c) 1-(cyclopropylmethyl)-4-(2'-(4"-chlorophenyl)-2'-oxoethyl) piperidine (d) 1-(cyclopropylmethyl)-4-(2'-(4"-chlorophenyl)-2'-oxoethyl) piperidine, hydrobromide salt (e) 1-(cyclopropylmethyl)-4-(4'-fluorophenoxymethyl)piperidine (f) 1-(cyclopropylmethyl)-4-(4'-fluorophenoxymethyl)piperidine, hydrochloride salt (g) 1-(cyclopropylmethyl)-4-(4'-chlorophenoxymethyl)piperidine (h) 1-(cyclopropylmethyl)-4-(4'-chlorophenoxymethyl)piperidine, hydrochloride salt (i) 1-(cyclopropylmethyl)-4-(4'-nitrophenoxymethyl)piperidine (j) 1-(cyclopropylmethyl)-4-(2'-(4"-biphenyl)-2'-oxoethyl)piperidine (k) 1-(cyclopropylmethyl)-4-(2'-(4"-biphenyl)-2'-oxoethyl)piperidine, hydrobromide salt.

Pharmaceutical compositions comprising an effective amount of a compound of Formula I or II and a pharmaceutically acceptable carrier are useful in the method of the present invention.

The preparation of the 1-cycloalkyl piperidine compounds of Formula II is described in copending, commonly assigned U.S. patent application Ser. No. 07/570199, filed Aug. 20, 1990, the disclosure of which is hereby incorporated by reference. The compound referred to herein as Ex. No. 504 is designated as the compound of Example No. 504 in U.S. Pat. application Ser. No. 07/570199.

The preparation of the (N-phthalimidoalkyl) piperidine compounds of Formula I is described in copending, commonly assigned U.S. patent application Ser. No. 07/602024, filed Oct. 23, 1990, the disclosure of which is hereby incorporated by reference. The compound referred to herein as Ex. No. 3 is referred to as Example No. 3 in U.S. Pat. application Ser. No. 07/602024.

Other sigma receptor antagonists lacking or having relatively weak dopamine receptor blocking activity are expected to be useful in the method of the present invention. Examples of other sigma receptor antagonists having greater affinity for sigma receptors than for dopamine receptor which are expected to be useful in the present invention are rimcazole (also known as BW234U) (Ferris et al. (1982) J. Pharm. Pharmacol. 34: 388–390; Ferris et al. (1986) Life Sciences 38: 2329–2337; U.S. Pat. No. 4,400,383; U.S. Pat. No. 4,588,728), remoxipride (Ogren et al. (1984) European Journal of Pharmacology 102: 439–474; U.S. Pat. No. 4,232,037; Snyder and Largent (1989) J. Neuropsychiatry 1: 7–15), and BMY14802 (Taylor and Dekleva (1987) Drug Development Research 11: 65–70; U.S. Pat. No. 4,605,655). The above identified patents are hereby incorporated by reference.

Other sigma receptor antagonists lacking or having relatively weak dopamine receptor blocking activity and expected to be useful in the method of the invention include the compounds of copending, commonly assigned U.S. patent applications Ser. No. 07/506961, filed Mar. 28, 1990 and U.S. Pat. application Ser. No. 07/500573, filed Mar. 28, 1990, the disclosures of which are hereby incorporated by reference.

EXAMPLE 1

The typical dopamine antagonist antipsychotic haloperidol is very active in mouse and rat tests predictive of therapeutic antipsychotic activity and in tests predictive of side-effect liability. We tested the combination of the representative sigma receptor antagonist Ex. No. 3 and haloperidol in a test predictive of antipsychotic therapeutic effects (inhibition of conditioned avoidance) and a test predictive of antipsychotic side-effect liability (induction of catalapsy). In this set of experiments haloperidol alone at 0.4 mg/kg p.o. inhibited conditioned avoidance behavior by 45%. However, in combination with Ex. No. 3 (3.8 mg/kg p.o.) haloperidol inhibited conditioned avoidance behavior by 85% ($p<.01$). Ex. No. 3 at this dose alone does not inhibit conditioned avoidance behavior.

Haloperidol produces a dose related (0.3 to 3.0 mg/kg p.o.) induction of catalepsy ($ED_{50}=1.13$ mg/kg p.o.). The addition of Ex. No. 3 (3.8 mg/kg p.o.) did not significantly change the cataleptogenic response to haloperidol at any dose.

These results indicate that Ex. No. 3 enhances the therapeutic efficacy of dopamine receptor antagonist antipsychotic agents, such as haloperidol, without altering the side-effect liability, thus enhancing the therapeutic index of haloperidol and lending greater safety to its clinical use. This is very significant for the treatment of psychosis, as it is the sideeffects associated with the typical antipsychotic agents that are the major limitation to their use.

Materials and Methods

Conditioned Avoidance and Escape Response: A modification of the method of Cook and Weidley (1957) was used. The apparatus is a Coulbourn Instrument large modular test cage measuring 10"×11"×12" with a pole suspended from the top center and a grid floor connected to a Coulbourn Instrument programmable shocker delivering a 0.75 mA pulsed current. The animals, male CDF rats (Charles River) weighing 250–350 g, are trained to a high degree of avoidance in a paradigm where they are required to climb the pole to avoid a footshock. Each animal is run 3 trials a day, 1 trial 30 min after drug administration, 1 trial 60 min after drug administration and 1 trial 90 min after drug administration. A trial consists of the animal being placed in the cage, after 10 sec the footshock comes on for 15 seconds. The animal is then removed from the cage. The animal is considered to have avoided the footshock when it climbs the pole within the first 10 sec of being placed in the cage (before the shock comes on). The animal is considered to have escaped when it climbs the pole during shock delivery. The animal is considered to have omitted when it fails to climb the pole during the trial.

Induction of Catalepsy: A modification of the method of Costall and Naylor (1975) was used. Rats, male CD rats (Charles River) weighing 250–300 g, are treated with test drugs and standards and tested for the presence of catalepsy 30 min, 60 min, and 90 min after treatment. To test for catalepsy each rat is placed with its front paws over a 10 cm high horizontal bar. The intensity of catalepsy is measured by the length of time it takes the animal to move both forelegs to the table. A time of 20 sec is considered maximal catalepsy.

Ex. No. 3 fumarate is suspended in 0.25% methycellulose. Haloperidol is dissolved in glacial acetic acid.

Both compounds are injected p.o. at a rate of 0.1 ml/100 gm body weight. The data reported is for 60 min pretreatment. All doses and $ED_{50}$'s are expressed as the free base equivalent.

Catalepsy data was analyzed using Kruskal-Wallis and Mann-Whitney U Tests. $ED_{50}$'s were calculated using Litchfield-Wilcoxen. Conditioned avoidance behavior was analyzed by the Fisher Exact Test.

As shown in Table 1, Ex. No. 3 at 3.8 mg/kg p.o. significantly ($p < 0.01$) potentiated the effect of haloperidol (0.4 mg/kg p.o.) on inhibition of conditioned avoidance responding in the rat. Therefore, Ex. No. 3 potentiated a measure of the therapeutic efficacy of the typical antipsychotic haloperidol.

TABLE 1

The effect of Ex. No. 3 + haloperidol on conditioned avoidance responding in the rat. Ex. No. 3 and haloperidol are given p.o. 60 min. before testing. Animals are trained to avoid a footshock in a pole climb apparatus.

| Treatment | N | % Antagonism of Avoidance |
| --- | --- | --- |
| haloperidol, 0.4 mg/kg + Vehicle | 20 | 45 |
| haloperidol, 0.4 mg/kg + Ex. No. 3., 3.8 mg/kg | 20 | 85* |

*p = .008: Fisher Exact Test

EXAMPLE 2

We tested the combination of the sigma receptor antagonist Ex. No. 504 and the typical antipsychotic haloperidol in a test predictive of antipsychotic therapeutic effects (inhibition of conditioned avoidance) and a test predictive of antipsychotic sideeffects liability (induction of catalypsy).

In this set of experiments haloperidol at 0.4 mg/kg p.o. did not inhibit conditioned avoidance behavior. However, in combination with Ex. No. 504, 3.9 mg/kg p.o., haloperidol inhibited conditioned avoidance behavior by 60% ($p < 0.01$). Ex. No. 504 at this dose alone does not inhibit conditioned avoidance behavior.

Haloperidol produced a dose related (0.3 to 3.0 mg/kg p.o.) induction of catalepsy ($ED_{50} = 0.88$ mg/kg p.o.). The addition of Ex. No. 504, 3.9 mg/kg p.o., antagonized or did not significantly change the cataleptogenic response to haloperidol at any dose.

These results suggest that Ex. No. 504 enhances the therapeutic efficacy of typical dopamine antagonist antipsychotic agents like haloperidol without altering the side-effect liability, thus enhancing the therapeutic index of haloperidol and lending greater safety to its clinical use.

Materials and Methods

The same materials and methods were used to evaluate Ex. No. 504 in conditioned avoidance response and the induction of catalepsy as described in Example 1.

Ex. No. 504 HBr is suspended in 0.25% methycellulose. Haloperidol is dissolved in glacial acetic acid. Both compounds are injected p.o. at a rate of 0.1 ml/100 gm body weight. The data reported is for 60 min pretreatment. All doses and $ED_{50}$'s are expressed as the free base equivalent.

As shown in Table 2, Ex. No. 504 at 3.9 mg/kg p.o. significantly ($p < 0.01$) potentiated the effect of haloperidol (0.4 mg/kg p.o.) on the inhibition of conditioned avoidance response in the rat.

TABLE 2

The effect of Ex. No. 504 + haloperidol on conditioned avoidance responding in the rat. Ex. No. 504 and haloperidol are given p.o. 60 min. before testing. Animals are trained to avoid a footshock in a pole climb apparatus.

| Treatment | N | % Antagonism of Avoidance |
| --- | --- | --- |
| haloperidol, 0.4 mg/kg + vehicle | 10 | 0 |
| haloperidol, 0.4 mg/kg + Ex. No. 504, 3.9 mg/kg | 10 | 60* |

*p = .005: Fisher Exact Test

EXAMPLE 3

The effect of the sigma receptor antagonist Ex. No. 504 in affecting the dose response curve of haloperidol in the conditioned avoidance response (pole climb) was tested. Ex. No. 504 (3.9 mg/kg p.o.) produced a statistically significant 3-fold lowering in the $ED_{50}$ (more potent) of haloperidol for inhibition of avoidance behavior, with no significant change in the $ED_{50}$ of haloperidol for inhibition of conditioned escape behavior (FIG. 1). The $ED_{50}$ of haloperidol alone for inhibition of conditioned avoidance behavior was 0.94 mg/kg p.o. In combination with Ex. No. 504 (3.9 mg/kg p.o.) the $ED_{50}$ of haloperidol was 0.32 mg/kg p.o.

The $ED_{50}$ of haloperidol alone for inhibition of escape behavior was 11.5 mg/kg p.o. and the addition of Ex. No. 504 (3.9 mg/kg p.o.) did not produce a significant change in the effect of haloperidol on conditioned escape behavior.

Inhibition of conditioned avoidance behavior is considered reflective of psychotherapeutic properties and inhibition of conditioned escape behavior is considered reflective of the unwanted sedative and motor incapacitation side effects produced by typical antipsychotic drugs like haloperidol. Ex. No. 504 does not inhibit conditioned avoidance or escape behavior by itself.

These results suggest that sigma receptor antagonists, such as Ex. No. 504, selectively enhance the therapeutic efficacy of typical dopamine antagonist antipsychotic agents like haloperidol without effecting certain side-effects, thus enhancing the therapeutic index of the antipsychotic agent. The addition of a sigma receptor antagonist, such as Ex. No. 504, to treatment with the typical dopamine receptor antagonist antipsychotics, such as haloperidol, is expected to selectively enhance the therapeutic efficacy and therefore produce a greater therapeutic index than the dopamine receptor antagonist antipsychotic alone.

Dosage Forms

Daily dosage ranges from 1 mg to 2000 mg. Dosage forms (compositions) suitable for administration ordinarily will contain 0.5-95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or entericcoated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Co., a standard reference text in this field.

What is claimed is:

1. A method of treating psychosis in a mammal comprising administering to the mammal: (a) an effective amount of a dopamine receptor antagonist selected from the group consisting of haloperidol and haloperidol decanoate and (b) a sigma receptor antagonist having the formula:

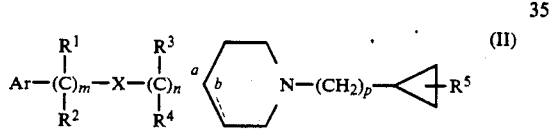

or a pharmaceutically acceptable salt thereof, wherein:
m is 0 to 3;
n is 0 to 3;
provided that m and n are not both 0;
p is 0 to 3;
X is O, S, SO, $SO_2$, $NR^6$, $CR^7R^8$, C(=O), or CHOH;
$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;
$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;
provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;
$R^5$ is H, alkyl, halogen, OH or alkenyl;
$R^6$ is H, alkyl of 1 to 5 carbon atoms or $Ar^1$;
Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;
$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;
$R^9$, $R^{10}$, $R^{11}$, $R^{12}$ and $R^{13}$ independently are H, alkyl of 1 to 5 carbon atoms or phenyl of $R^{10}$ and $R^{11}$ taken together are an alkylene chain of 3 to 6 carbon atoms or $R^{12}$ and $R^{13}$ taken together are an alkylene chain of 3 to 6 carbon atoms; and
a or b is a double bond or a single bond, provided that both are not double bonds.

2. A method of claim 1 wherein:
X is CO, CHOH or O;
m is O;
n and p are 1;
$R^3$–$R^5$ are H; and/or
Ar is phenyl optionally substituted with halogen, $OCH_3$, $NH_2$, $NO_2$ or another phenyl group.

3. A method according to claim 1 wherein the compound is 1-(cyclopropylmethyl)-4-(2'-(4''-fluorophenyl)-2'-oxoethyl) piperidine.

4. A method according to claim 1 wherein the compound is 1-(cyclopropylmethyl)-4-(2'-(4''-chlorophenyl)-2'-oxoethyl) piperidine.

5. A method according to claim 1 wherein the compound is 1-(cyclopropylmethyl)-4-(4'-fluorophenoxymethyl) piperidine.

6. A method according to claim 1 wherein the compound is 1-(cyclopropylmethyl)-4-(4'-chlorophenoxymethyl)piperidine.

7. A method according to claim 1 wherein the compound is 1-(cyclopropylmethyl)-4-(4'-nitrophenoxymethyl) piperidine.

8. A method according to claim 1 wherein the compound is 1-(cyclopropylmethyl)-4-(2'-(4''-biphenyl)-2'-oxoethyl)piperidine.

* * * * *